United States Patent [19]

Sklebitz

[11] Patent Number: 4,817,125
[45] Date of Patent: Mar. 28, 1989

[54] RADIO-DIAGNOSTIC EQUIPMENT WITH SHUTTER

[75] Inventor: Hartmut Sklebitz, Erlangen, Fed. Rep. of Germany

[73] Assignee: Siemens Aktiengesellschaft, Berlin and Munich, Fed. Rep. of Germany

[21] Appl. No.: 52,677

[22] Filed: May 20, 1987

[30] Foreign Application Priority Data

Jun. 30, 1986 [DE] Fed. Rep. of Germany ....... 3621868

[51] Int. Cl.⁴ .............................................. G21K 1/04
[52] U.S. Cl. .................................... 378/152; 378/150; 378/151
[58] Field of Search .................. 378/99, 205, 147–152, 378/156–158, 153; 358/111

[56] References Cited

U.S. PATENT DOCUMENTS

| | | | |
|---|---|---|---|
| 3,448,270 | 6/1969 | Peyser | 250/105 |
| 3,631,249 | 12/1971 | Friede et al. | 250/86 |
| 3,655,963 | 4/1972 | Brunnee et al. | 250/281 |
| 3,912,936 | 10/1975 | Cunninghame et al. | 250/512 |
| 4,659,544 | 4/1987 | Sawayama et al. | 376/451 |
| 4,672,652 | 6/1987 | Huttenrauch et al. | 378/152 |
| 4,715,056 | 12/1987 | Vlasbloem et al. | 378/152 |
| 4,739,173 | 4/1988 | Blosser et al. | 378/152 |
| 4,754,147 | 6/1988 | Maughan et al. | 378/152 |

FOREIGN PATENT DOCUMENTS

| | | |
|---|---|---|
| 0114369 | 8/1984 | European Pat. Off. . |
| 0158382 | 10/1985 | European Pat. Off. . |
| 0162512 | 11/1985 | European Pat. Off. . |
| 1800879 | 5/1970 | Fed. Rep. of Germany . |
| 2024796 | 12/1971 | Fed. Rep. of Germany ...... 378/150 |
| 2053089 | 5/1972 | Fed. Rep. of Germany . |
| 2905202 | 8/1980 | Fed. Rep. of Germany . |
| 2146790 | 4/1985 | United Kingdom . |

OTHER PUBLICATIONS

Journal "METALL" 39, 1, 1985, pp. 34–38; Jan. issue., (* corresponds to U.S. Pat. No. 3,631,249).

Primary Examiner—Carolyn E. Fields
Assistant Examiner—Joseph A. Hynds
Attorney, Agent, or Firm—Lawrence C. Edelman

[57] ABSTRACT

Radio-diagnostic equipment includes an X-ray tube and a shutter which defines an aperture of modifiable size for allowing X-rays to pass therethrough. The shutter consists of a plurality of individual lamella which lie adjacent each other about the sides of the aperture and can be adjusted individually in a longitudinal direction depending on the size of the object under examination. An X-ray image intensifier and a television camera coupled to it generate a video signal and a monitor reproduces an image of the video signal. An evaluating circuit derives a control signal from the video signal which is applied to a position adjusting device including spring-like elements which can be deflected from an initial position by physical forces for controlling the positioning of each lamella.

16 Claims, 2 Drawing Sheets

RADIO-DIAGNOSTIC EQUIPMENT WITH SHUTTER

BACKGROUND OF THE INVENTION

1. Field of the Invention

The invention concerns radio-diagnostic equipment including an X-ray tube and a shutter for defining an aperture of modifiable size through which the X-ray radiation can pass. The shutter consists of a plurality of lamellae which lie adjacent to each other at the sides of the aperture and are independently positionable in a longitudinal direction depending on the size of the object to be examined. An X-ray image intensifier is coupled to a television camera for generating video signals which are applied to a monitor for reproduction of the video signals. An evaluation circuit also responsive to the video signals applies control signals to a position regulating device for controlling the position of the individual lamellae.

2. Description of the Prior Art

U.S. Pat. No. 3,631,249 describes a primary radiation shutter for radio-diagnostic equipment in which a semi-transparent shutter consisting of two shutter plates attenuates the lateral radiation in a beam of X-rays which otherwise, especially in the case of extremities, fall full strength onto the X-ray image intensifier input for the fluorescent screen and thus produce light areas which impair the recognition of details in the actual area under examination. The use of semi-transparent shutter plates attenuates these irradiated lateral areas so that visibility in the areas under observation is increased and furthermore, contrasting objects, for example, surgical instruments which are advanced from the sides of the area under examination, are still clearly visible. To adjust the position of the object under examination with respect to the radio-diagnostic equipment, the shutter plates are placed on a rotatable shutter disk. To adjust the width of the unimpaired path of the X-rays, both shutter plates can be moved toward each other until, for example, all irradiated areas have disappeared. In the case of curvilinear contours, as is normally the case, no adjustment to contours can be obtained with these rectilinear frontal edges of the shutter plates. Either a large part of the object to be examined is also attenuated in the process or large parts of the television image are still irradiated and the recognition of details continues to be reduced.

Furthermore, from DE-OS No. 29 05 202 an illuminated light viewing box is shown for viewing transparent rectangular pictures. The area on which the picture is placed can be darkened by adjustment of a plurality of parallel narrow width cover strips. By placing the pictures on the edge of the light viewing box their size is automatically perceived. Initially the strips prevent illumination of the picture. Thereafter, only those strips which cover the picture are moved, via a motor, until the film is illuminated up to its lower edge. Several films can only be simultaneously illuminated if their vertical dimensions are identical. This, however, means also that an alignment to irregular contours by the lamellae of this light viewing box is not possible.

One object of the invention is to create radio-diagnostic equipment of the kind mentioned above in which the semi-transparent shutter adjusts as precisely as possible to the contours of the object under examination so that none or only small areas of the examined object are covered or only small areas in the vicinity of the object are not covered.

SUMMARY OF THE INVENTION

In accordance with the principles of the invention the device which regulates the position of the individual lamellae of the shutter has spring elements which by physical means can be deflected from an initial position. In this way, it is possible through a simple mechanical construction to individually move the lamellae of the shutter simultaneously toward each other until each lamella touches the outer contours of the object under examination.

A simple process for adjusting the lamellae is described in a preferred embodiment wherein the spring elements consist of flexible strips which are, for example, of bimetal sheets or shape memory alloys. Such shape memory alloys are well known and described, for example, in the journal "Metall", 39, 1, 1985, pages 34 to 38. Spring elements produced from these alloys can be permanently deformed at low temperatures. By heating these elements above a certain temperature, they again assume their original shape. An individual simultaneous control of each lamella can take place when each lamella has a flexible strip assigned to it.

An advantageous design of an evaluation circuit is described including a circuit to determine the position of the lamellae within the video image into which the clock pulses of a television camera and control signals which characterize each selected lamellae are fed. The video signal is carried to an adaptation stage. The adaptation stage and the position circuit are connected to a gate circuit to which a peak value detector is connected. The output signal of the detector is applied to two comparison stages which compare it to adjustable threshold values. A first counter is connected to the comparison stages which is connected to a further comparison stage which compares the output signal of the first counter with that of a second counter The further comparison stage controls the spring elements It has proven to be of advantage that the lamellae are arranged in parallel next to each other at both sides of the slit of the X-ray aperture The aperture can be adjusted to any desired shape if the lamellae are directed radially toward the aperture Rotation of the shutter can be omitted if the shutter consists of two shutter systems perpendicular to each other each system having a plurality of individual lamellae. Disruptive adaptation processes with repeated radiographic procedures are not necessary if in a radiographic pause the first counter stores its last value when it is stopped.

Other features and advantages of the invention will be apparent from the following description of the preferred embodiment and from the claims.

For a fuller understanding of the present invention, reference should now be made to the following detailed description of preferred embodiment of the invention and to the accompanying drawings.

DETAILED DESCRIPTION OF THE INVENTION

Figure 1:
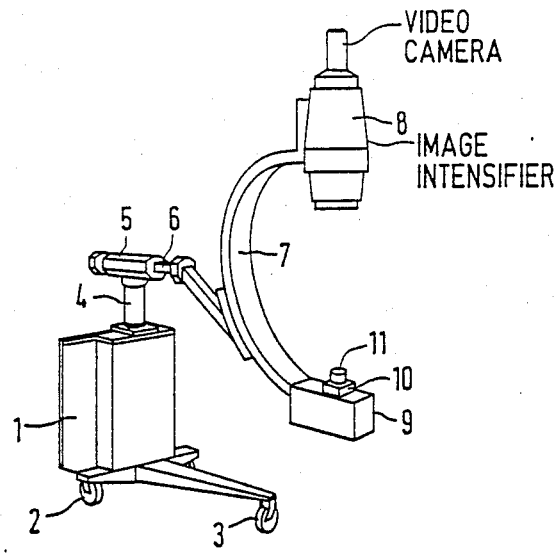
FIG. 1 illustrates radio-diagnostic equipment having a primary radiation shutter.

FIG. 1 shows radio-diagnostic equipment 1, movable with wheels 2 and 3, which finds multiple uses in surgical applications. Equipment 1 comprises a vertical support 4 the height of which can be adjusted using a shifter collar 5 in which an adjustable horizontal support 6 rests. A C-arc 7 which can also be slidably adjusted is connected at the end of horizontal support 6. A housing 8 for an X-ray image intensifier and a television camera are attached to one end of C-arc 7 and at the other end a housing 9 for an X-ray tube is attached. X-ray tube housing 9 is equipped with a primary radiation shutter 10 upon which a tubular structure 11 is fastened.

Figure 2:
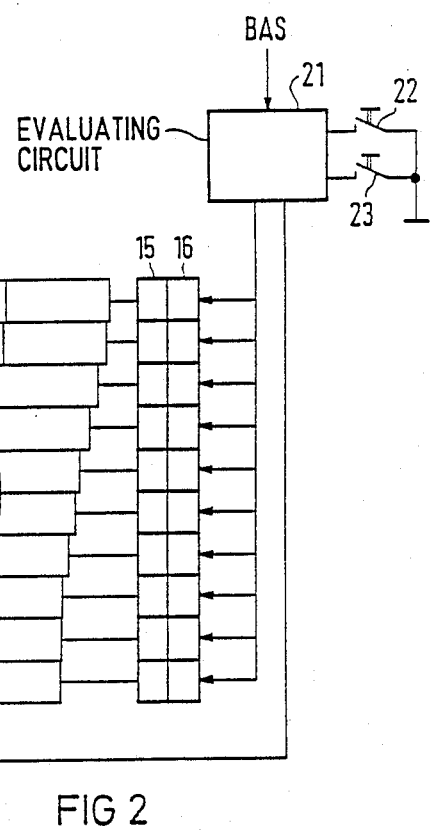
FIG. 2 illustrates a schematic design of the FIG. 1 shutter constructed according to the principles of the invention.

FIG. 2 shows the schematic structure of a semitransparent shutter 12 which is located in primary radiation shutter 10. Shutter 12 consists of a plurality of parallel strip-like lamellae 13 arranged side by side in two opposing groups which have at their distal ends an absorption value which corresponds to an iron plate having a thickness of 0.4 mm to 3.5 mm thick. The lamellae can also comprise non-transparent lead. Instead of a parallel arrangement of lamellae 13, it is possible to arrange them circularly, each radially pointing inward. In this way, objects of any shape can be adjusted to without difficulty.

Lamellae 13 are mechanically connected to flexible strips 15 which serve as spring elements, which are shown here only schematically, the other side of which is held firmly in position (for purposes of simplification only one side is shown). By physical means, especially heat, flexible strips 15 can be moved out of their starting position so that lamellae 13 can be moved toward each other from the opened initial position. Filament resistors 16 are associated with respective ones of flexible strips 15 so as to cause a warming of the flexible strips. Flexible strips 15 can be designed in such a way that an electric current can be used to heat them.

Shutter arrangement 12 is connected to a shutter ring 17 which has on its outer edge tooth segments 18 into which an endless screw 20 meshes as driven by a motor 19 so that the entire shutter 12 can be rotated around its center. Instead of the position adjustment of shutter 12 through rotation of shutter ring 17, two equal shutter systems can be used which are placed a short distance behind each other in the direction of the radiation so that individual lamellae of the shutter systems are perpendicular to each other.

An evaluation circuit 21 receives the baseband (BAS) video signal from the video camera and controls motor 19 and flexible strips 15. Furthermore, two push-button switches 22 and 23 are connected to evaluation circuit 21 for controlling the automatic opening and closing of shutter 12. Circular field 24 indicates the area irradiated with X-rays and corresponds to the image reproduced on a monitor (not shown) of the X-ray television chain. The knee joint of a patient is illustrated as an object 25 to be examined.

In its initial position, shutter 12 is opened maximally; all lamellae 13 are outside of field 24. At the beginning of the radiography, after push button switch 22 is pushed, flexible strips 15 are controlled by the evaluation circuit 21 so that the lamellae 13 move toward each other and shutter 12 slowly closes. Depending on the BAS video signal, the individual flexible strips 15 are controlled by the evaluation circuit 21 in such a way that they remain in position if a certain preset level of brightness of the BAS video signal associated with a given lamellae falls below a certain previously chosen level of brightness. If the object 25 under examination moves, the individual lamellae follow the movement correspondingly by either opening or closing further.

The control of motor 19 through evaluation circuit 21 causes a rotation of the shutter ring 17 so that orientation of the slit of shutter 12 is adjustable with respect to the examined object 25. At the end of the radiography, after push button 23 is pushed, flexible strips 15 are driven by evaluation circuit 21 in such a way that shutter 12 is again completely opened. In this opening process, however, as will be described in detail later, the last setting of the lamellae 13 can be stored, so that by pushing push button 22 they can assume the position at the beginning of the next radiographic procedure which they had at the end of the prior radiographic procedure. The lamellae 13 can, however, be so controlled that they remain during the pauses of radiographic procedure in the position shown. In this way, a new positioning process with great loss of image quality at the beginning of the next radiographic procedure is avoided. Additionally, such a repositioning process could represent a highly disturbing process for the operator during the radiographic procedure.

Figure 3:
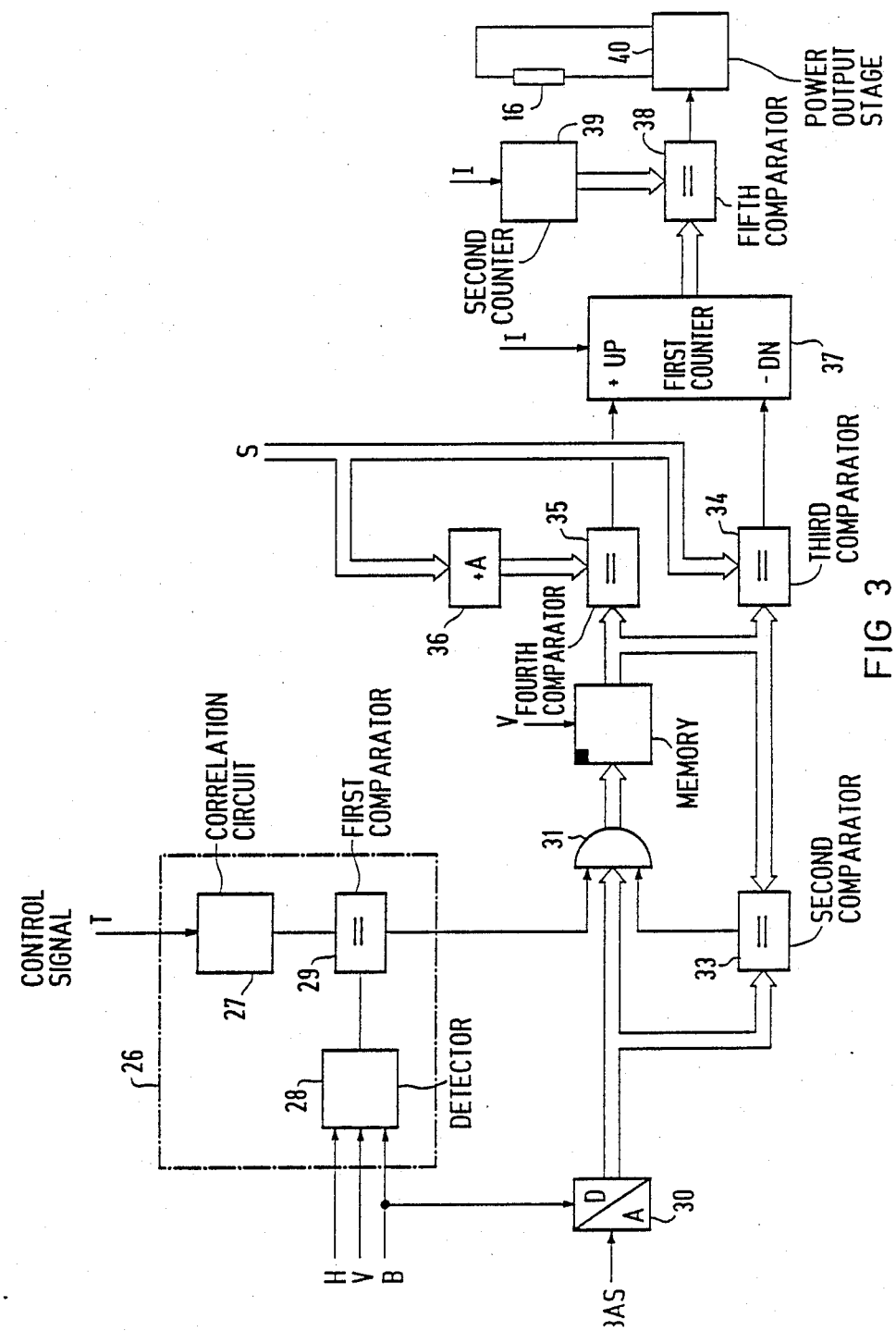
FIG. 3 illustrates a block diagram of the evaluation circuit shown in FIG. 2.

In FIG. 3, evaluation circuit 21 is shown which includes a circuit 26 for determining the position of lamellae 13 within the video image. Evaluation circuit 21 causes coordination of the actual BAS video signal with the individual lamellae 13. It contains a correlation circuit 27 which correlates the areas to be covered with the individual lamellae 13. Circuit 27 can, for example, comprise a memory which contains these areas. A control signal (T) is applied to circuit 27 which identifies the just previously selected lamellae. A detector 28 also contained in circuit 26 is responsive to the horizontal (H) and vertical (V) pulses as well as the picture element clock (B) of the television chain and serves to determine the actual position at any given time of the scanned BAS video signal. The output signals of circuit 27 and of detector 28 are fed into a first comparator 29 which generates an output signal if at any given time the BAS video signal lies within the area of the selected lamela 13.

The BAS video signal is also applied to an analog/digital (A/D) converter 30 which functions as an adaptation stage and into which the picture element clock signal B is fed for digitalization of the BAS video signal. The digital output signal of A/D converter 30 is applied to an AND gate 31 which functions as a gate circuit. The digital output signals from A/D converter 30 are passed by AND gate 31 only after circuit 26 has determined that the incoming BAS video signal belongs to the lamella 13 selected at that time. The output of AND gate 31 is connected to a memory 32, the output of which is applied to a second comparator 33. A second input of comparator 33 receives the digitized video signal from A/D converter 30. Second comparator 33 generates an output signal which is applied to AND gate 31 whenever a new picture element of the video signal is greater than a prior picture element supplied from memory 32, such that at the end of each television scanning interval the maximum amplitude value contained in the video signal of the area assigned to the selected lamella 13, which corresponds to the brightest picture element, is always present in memory 32. In this way, memory 32, second comparator 33, and AND gate 31 function as a peak value detector. The vertical pulses V erase memory 32 after each complete television image so that the maximum value can again be determined.

The output of memory 32 is subsequently applied to a first input of third and fourth comparators 34 and 35. An adjustable threshold value S is applied to a second input of comparator 34 and the threshold value S, increased by an amount A in an addition stage 36, is applied to a second input of comparator 35. The output signals of the third and fourth comparators 34 and 35 are connected to UP and DN control inputs of a first counter 37 in such a way that first counter 37 counts counting pulses I downward when third comparator 34 supplies its output signal and counting upward when fourth compartor 35 supplies its output signal. The output of first counter 37 is connected to first input of a fifth comparator 38, the second input of which receives the output of a second counter 39. Fifth comparator 38 is connected to a power output stage 40 to which filament resistors 16 assigned to flexible strips 15 are connected.

Below, the function of evaluating circuit 21 is explained using an example. For the sake of simplicity, only one of lamellae 13 is considered. At the beginning of the radiographic process a High H-signal is supplied by circuit 26 as long as the picture element supplied by A/D converter 30 is within the area in the television image belonging to the presently selected lamella 13. Since at the beginning no value is as yet contained in memory 32, second comparator 33 also supplies an H-signal so that the first picture element is read into memory 32. This continues within the area belonging to the selected lamella 13 until the maximum value of the picture elements are contained in memory 32 and picture elements which are equal to or smaller than the stored picture elements are blocked by the application form second comparator 33 of a logic Low L-signal applied to AND gate 31.

If the value of the stored picture element is greater than the set threshold value S increased by A, fourth comparator 35 supplies an output signal so that the count indicated by first counter 37 is increased. In this way, the filament resistor 16 belonging to the selected lamella 13 is exited and the selected lamella 13 is moved by the flexible strip 15 so that shutter 12 closes in this area. The vertical pulse V erases memory 32 so that for the next television image the maximum value can again be read into memory 32. This continues until the lamellae 13 approaches the object 25 under examination so that from now on, the maximum value of the picture elements within the area of the lamellae 13 decreases. If the maximum value is less than the threshold value S increased by A which is applied to the fourth comparator 35, the filament resistor 16 of the selected lamellae 13 is not increasingly exited so that the lamellae 13 remains in the semi-closed position. The remaining lamellae 13 are controlled in the same manner so that, for example, they assume the position illustrated in FIG. 2.

If, however, the maximum value contained in memory 32 of the picture element is less than the threshold value S as, for example, can be the case after some movement by the object 25 under examination, then third comparator 34 supplies an output signal so that the count indicated by first counter 37 is decreased. Thereby, the power to filament resistor 16 is decreased so that its temperature decreases and the flexible strip 15 continues to open further.

The outputs of comparators 34 and 35 decrease or increase the count indicated by counter 37 into which counting pulses I of any kind are fed. For this purpose, television set-up pulses or pulses of a free running oscillator can be used. Via fifth comparator 38 and continuously running counter 39, which counts continuously from zero to a maximum value corresponding to the maximum value of first counter 37, the digital count of first counter 37 is converted into a signal having a different pulse-pause ratio. As long as the count indicated by second counter 39 is smaller than that of counter 37, an H-signal is generated at fifth comparator 38 while an L-signal is generated at the output of fifth comparator 38 when the count indicated by second counter 39 has surpassed that of first counter 37. In response to this H or L output signal of fifth comparator 38, the filament resistors 16 in power output stage 40 are driven with a corresponding heater current so that a predetermined temperature is obtained which can appropriately deflect the flexible strips 15 so that lamellae 13 remain in the position shown.

In pauses during the radiographic process, counting by first counter 37 is stopped so that the value of the last count indicated remains stored and lamellae 13 stay in their last assumed position. It is, however, possible to set the signal of fifth comparator 38 which is fed into the power output stage 40 to an L-level which can then, for example, shortly before the end of the radiographic pause, be released so that lamellae 13 at the beginning of the continued radiography are again appropriately closed.

During the pauses in driving filament resistors 16, their resistances can be measured and compared to the resistance value present immediately before switching off the radiographic process and maintained at a constant value via a regulating circuit. A second specific measuring resistance can be applied at flexible strips 15 as a temperature measuring resistance.

For alternating the drive control of filament resistors 16 and lamellae 13 in a multiplex operation, for each of lamellae 13 at least the location in memory 32, and third and fourth comparators 34 and 35 have to be provided. Through a multiplex circuit which is required under these circumstances, the output signal of AND gate 31 is fed to the corresponding location of memory 32 and the output signal of this location in memory 32 is fed to second comparator 33 as well as third and fourth comparators 34 and 35. In this way, an almost simultaneous changing of position of lamellae 13 takes place so that shutter 12 closes as far as is required along its entire width within the shortest possible time.

In order to ensure a rapid response of flexible strips 15 even during motion in which the lamellae 13 are supposed to be opened, it is advisable to allow a ventilator to ventilate flexible strips 15 constantly and evenly with ambient air.

Thus, there has been shown and described novel apparatus for shuttering radio-diagnostic equipment which fulfills all the objects and advantages southt therefore. Many changes, modifications, variations and other uses and applications of the subject invention will, however, become apparent to those skilled in the art after considering this specification and the accompanying drawings which disclose only a preferred embodiment thereof. For example, the threshold value S fed into third comparator 34 can be continously set by the operator. It is also possible to represent organs appropriately if the threshold value can be selected via push buttons dependent on the organ. Furthermore, rotation of shutter ring 17 and alignment of the slit of shutter 12 can be coupled with the television camera so that the longitudinal direction of the lamellae always lies in the line (horizontal) direction of the television chain. Alternatively, such orientation can also be undertaken by a similar evaluation of the television image from the BAS video signal. All such changes, modifications, variations and other uses and applications which do not depart from the spirit and scope of the invention are deemed to be covered by the invention which is limited only by the claims which follow.

What I claim is:

1. An X-ray apparatus, comprising:
   an X-ray tube for transmission of X-rays through an object under examination;
   imaging means responsive to said X-rays transmitted through said object for generating a video signal representative of an image corresponding to the attenuation of said X-rays transmitted through said object;
   a shutter arranged between said X-ray tube and said imaging means for providing an aperture of modifiable size through which said X-rays can pass, said shutter comprising a plurality of individual lamellae which lie adjacent to each other, are located about the sides of said aperture and are independently positionable in a longitudinal direction depending on the shape of the object under examination;
   an evaluation circuit means coupled to said imaging means and responsive to said video signal for generating control signals therefrom; and
   position regulating means responsive to said control signals for controlling the positioning of said individual lamella, said position regulating means comprising a plurality of spring-like elements coupled to said lamellae, each of said spring-like elements comprising an alloy having a shape memory and being deflectable so as to reposition said lamellae from an initial position, in response to supplied heat, to a second position, and back again substantially to said initial position in response to removal of said supplied heat.

2. Apparatus according to claim 1, wherein said imaging means comprises:
   an X-ray image intensifier for receiving said X-rays transmitted through said object; and
   a video camera coupled to said image intensifier for generating said video signal.

3. Apparatus according to claim 1, further including:
   heating means responsive to the position regulating means for controllably heating said spring-like elements so as to cause their deflection from said initial position.

4. Apparatus according to claim 2, further including:
   a monitor responsive to said video signal for reproducing said image corresponding to the attenuation of said X-rays.

5. Apparatus according to claim 2, wherein:
   each one of said lamella has one spring-like element coupled to it.

6. Apparatus according to claim 2, wherein:
   said evaluation circuit means comprises,
   a position determining circuit for correlating the position of each one of said lamellae with said video signal in response to clock signals of said video signal and from control signals which identify a selected one of said lamellae; and
   said position regulating means comprises,
   a converter stage responsive to said video signal for digitizing said video signal;
   a gate coupled to said position determinating circuit and said converter stage for providing a digital output signal;
   a detector responsive to said digital output signal for detecting the peak value of said video signal, said detector providing a detector output signal;
   a first counter for counting in response to applied pulses;
   a first comparison means for comparing said detector output signal with first and second threshold levels and in response to said comparing controls the counting of said first counter;
   a second counter for counting in response to applied pulses; and
   a second comparison means for comparing said counting of said first counter with said counting of said second counter for developing a position control signal which controls the positioning of said lamellae.

7. Apparatus according to claim 6, further including:
   heating means responsive to said position control signal of the position regulating means for controllably heating said spring-like elements so as to cause their deflection from said initial position.

8. Apparatus according to claim 2, wherein:
   said lamellae are arranged in parallel one next to the other and in two opposing groups on respective sides of a slit shaped aperture formed by said shutter.

9. Apparatus according to claim 2, wherein:
   said lamellae are aligned radially toward a circular shaped aperture formed by said shutter.

10. Apparatus according to claim 2, wherein:
    said shutter comprises two shutter systems each having a plurality of individual lamellae which are perpendicular to the lamellae of the other shutter system.

11. Apparatus according to claim 6, further including:
    means for stopping the counting of said first counter during a pause in a radiographic examination, wherein said first counter holds its last count.

12. An X-ray apparatus, comprising:
    an X-ray tube for transmission of X-rays through an object under examination;
    imaging means responsive to said X-rays transmitted through said object for generating a video signal representative of an image corresponding to the attenuation of said X-rays through said object;
    a shutter arranged between said X-ray and said imaging means for providing an aperture of modifiable size through which said X-rays can pass, said shutter comprising a plurality of individual lamellae which lie adjacent to each other, are located about the sides of said aperture and are independently positionable in a longitudinal direction depending on the shape of the object under examination;
    an evaluation circuit means coupled to said imaging means and responsive to said video signal for generating control signals therefrom; and
    position regulating means responsive to said control signals for controlling the positioning of said individual lamella, said position regulating means comprising a plurality of spring-like elements coupled to said lamellae, each of said spring-like elements comprising a bimetal sheet and being deflectable so as to reposition said lamellae from an initial position, in response to supplied heat, to a second position, and back again substantially to said initial position in response to removal of said supplied heat.

13. Apparatus according to claim 12, wherein said imaging means comprises:
an X-ray image intensifier for receiving said X-rays transmitted through said object; and
a video camera coupled to said image intensifier for generating said video signal.

14. Apparatus according to claim 12, further including:
heating means responsive to the position regulating means for controllably heating said spring-like elements so as to cause their deflection from said initial position.

15. Apparatus according to claim 13, further including:
a monitor responsive to said video signal for reproducing said image corresponding to the attenuation of said X-rays.

16. Apparatus according to claim 13, wherein:
each one of said lamella has one spring-like element coupled to it.

* * * * *